United States Patent [19]
Bell et al.

[11] 3,943,076
[45] Mar. 9, 1976

[54] FLAME RETARDANTS FOR PLASTIC FOAMS

[75] Inventors: Reuben H. Bell, Granville; Kevin M. Foley, Hebron, both of Ohio

[73] Assignee: Owens-Corning Fiberglas Corporation, Toledo, Ohio

[22] Filed: Jan. 27, 1975

[21] Appl. No.: 544,439

Related U.S. Application Data

[62] Division of Ser. No. 418,708, Nov. 23, 1973.

[52] U.S. Cl....... 260/2.5 AJ; 260/2.5 R; 260/2.5 F; 260/2.5 FP; 260/2.5 N; 260/2.5 H; 260/2.5 HB; 260/45.7 P; 260/DIG. 24

[51] Int. Cl.$^2$...................... C08G 18/14; C08J 9/00

[58] Field of Search................ 260/2.5 AJ, 45.7 P

[56] References Cited
UNITED STATES PATENTS 3,113,139   12/1963   Birum ............................... 260/2.5

*Primary Examiner*—H. S. Cockeram
*Attorney, Agent, or Firm*—John W. Overman; Patrick P. Pacella

[57] ABSTRACT

Addition products of polyepoxides which have proved to be excellent flame-retardants for plastic foams such as polyurethane foams are disclosed.

6 Claims, No Drawings

FLAME RETARDANTS FOR PLASTIC FOAMS

This is a division of application Ser. No. 418,708, filed Nov. 23, 1973.

This invention relates to flame retardants for plastic foams.

Plastic foams such as polyurethane foams have found widespread utility in the fields of insulation and structural reinforcement. One factor limiting the commercial utilization of polyurethane foams has been their flammability when exposed to flame or high temperatures. Various additives are known in the art for producing flame resistance in polyurethane foams. For example, the use of elementary sulfur as a flame-retardant in some plastic foams is disclosed in U.S. Pat. No. 3,542,701.

We now have discovered addition products of polyepoxides which have proved to be excellent flame-retardants for plastic foams such as polyurethane foams. The addition products of this invention are halogenated, and are phosphorus or silane substituted.

Accordingly, an object of this invention is to provide addition products of polyepoxides.

Another object of this invention is to provide polyurethane foams incorporating these polyepoxide addition products.

Other object, aspects and advantages of this invention will be apparent to one skilled in the art from the following disclosure and appended claims.

The addition products of this invention are represented by the formula:

$$\begin{array}{c} X \diagdown \diagup OY(O-CH_2-CH-R^2)_m \\ R^1 \\ \diagup \diagdown X \\ (R^2-CH-CH_2-O)_mYO \quad X \\ | \\ X \end{array}$$

wherein $R^1$ is a divalent group selected from alkyl, alkoxy, cycloalkyl, cycloalkoxy, aryl, an ester represented by the formula $$R^3-\overset{O}{\underset{\|}{C}}-O-R^3$$

wherein each $R^3$ is alkyl, alkoxy, cycloalkyl, cycloalkoxy or aryl, each $R^3$ having from 1 to 20 carbon atoms, or an ether represented by the formula $R^3-O-R^3$ wherein $R^3$ is as previously defined, or a combination thereof having from 1 to 50 carbon atoms; each $R^2$ is an alkyl radical having 1 to 20 carbon atoms, each X is chlorine, bromide or fluorine; one of Y is phosphorus, the radical

or silicon and the other Y is silicon and each $m$ is the integer 2 when Y is phosphorus or the radical PO and the integer 3 when Y is silicon. Preferably, each X is chlorine or bromine and each $R^2$ is an alkyl radical having 1 to 8 carbon atoms.

The polyepoxides employed in this invention contain at least 2 epoxide groups before the addition reactions are carried out. An epoxy resin used most widely is the epoxy resin made by condensing epichlorohydrin with bisphenol A. An excess of epichlorohydrin is used to leave epoxy groups on each end of the low molecular weight resin:

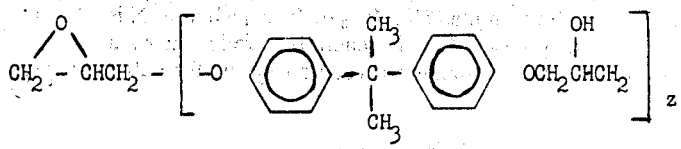

wherein $z$ is 0 to 3. Other specific examples of polyepoxides employed in this invention include:

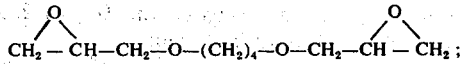

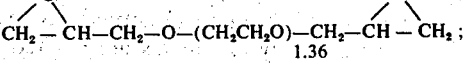

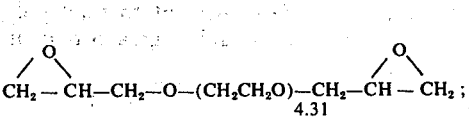

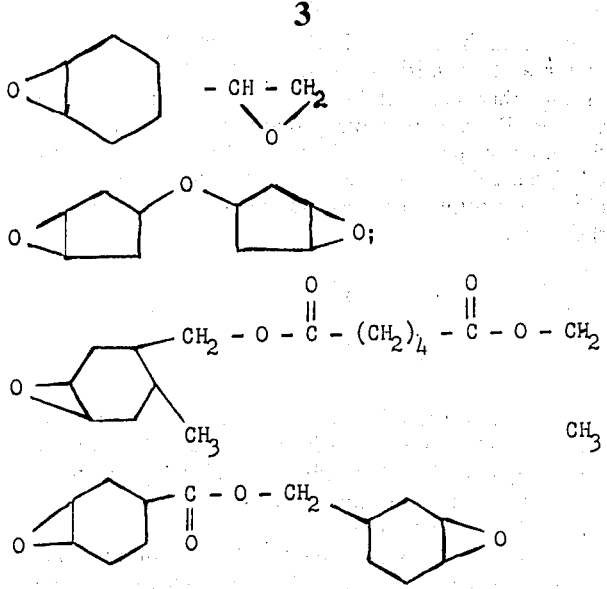

One method for preparing the addition products of this invention comprises reacting the polyepoxide with a compound represented by the formula:

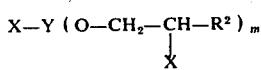

wherein each X, Y, R² and m are as previously defined. The resulting product, which has at least one epoxide group remaining, than is reacted with a halide represented by the formula $SiX_4$, $PX_3$ or $POX_3$ wherein X is as previously defined. This reaction is followed by a reaction with an epoxide represented by the formula.

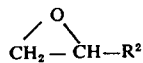

wherein $R_2$ is as previously defined.

As demonstrated by the following examples, the addition products of this invention are excellent flame-retardants for plastic foams such as polyurethane foams. This invention is applicable to foams or other cellular or porous structures of synthetic macromolecular substances. The most important foams or structures known at present are those of polystyrene and polyurethanes. Other cellular or porous structures include those of polyolefins, polyesters, polyethers and polyacetals.

The amount of flame retardant materials in the polyurethane foams, by weight, ranges from 0.5 to 25.0 percent, preferably 5.0 to 15.0 percent.

Urethanes or polyurethanes can be formed by a variety of methods, although the most widely used production method is the reaction or di- or polyfunctional hydroxyl compounds with di-polyfunctional isocyanates. The polyols and polyisocyanates are reacted in the presence of a suitable catalyst, a blowing agent and generally a surfactant. Both the one-shot technique and the pre-polymer approach can be employed. The amount of polyisocyanate used will vary slightly but in general the total — NCO equivalent to total polyol active hydrogen equivalent should be greater than one.

The advantages of this invention are illustrated by the following examples. The reactants, proportions and other specific conditions are presented as being typical and should not be construed to limit the invention unduly.

EXAMPLE I

This example demonstrates the preparation of the addition product:

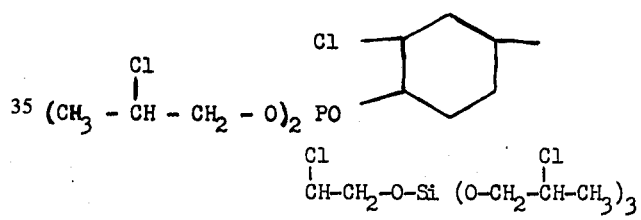

Silicon tetrachloride (1.0 mole) was placed in a 1 liter, 3 neck flask equipped with a stir bar, an addition funnel, reflux condenser and thermometer. With stirring, 210 ml of propylene oxide (3.0 moles) then was added to the flask. The flask was cooled in an ice bath during the propylene oxide addition. With stirring and cooling 1.0 mole of

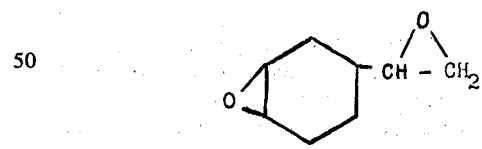

was added and followed by the addition of 1.0 mole of phosphorus trichloride. While continuing stirring and cooling, 2.51 moles of propylene oxide was added to the flask.

The mixture was kept at room temperature overnight and excess propylene oxide was removed under vacuum. The preparation was employed as a fire retardant in Example III.

EXAMPLE II

This example demonstrates the preparation of the addition product:

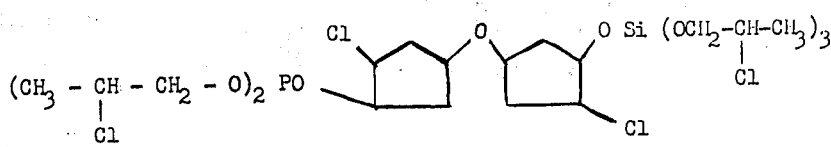

The process of Example I was repeated except that 1.0 mole of

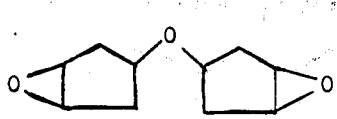

was employed instead of 1.0 mole of

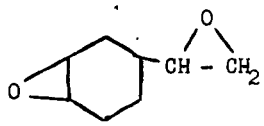

The preparation was employed as a fire retardant in Example IV.

EXAMPLE III

A polyurethane sample incorporating the addition product of Example I was prepared with the following ingredients.

| Ingredients | Parts by Weight |
| --- | --- |
| Isocyanate-polyphenyl polymethylene polyisocyanate | 95.2 |
| Polyol-75% oxyalkylated, resole based polyol and 25% dibromoneopentyl glycol | 72.7 |
| Polyol-propoxylated, diethylene triamine | 4.9 |
| Water | 0.8 |
| Surfactant-silicone glycol copolymers with direct silicone carbon bonds | 1.0 |
| Catalyst-triethylenediamine in dipropylene glycol | 0.6 |
| Blowing agent-trichlorofluoromethane | 20.0 |
| Addition Product of Example I | 10.0 |
| NCO/OH index | 1.1 |

The sample was prepared by the one-shot method comprising adding the surfactant and flame retardant material to the polyol. The blowing agent then was added followed by the water and catalyst. The run was completed by adding the isocyanate, mixing and dispensing the mixture and allowing the foam to rise into a continuous bun.

EXAMPLE IV

The process of Example III was repeated except that the addition product of Example II was employed instead of the addition product of Example I.

EXAMPLE V

The process of Example III was repeated except that no additive flame retardant material was employed, i.e., the addition products of Examples I and II.

EXAMPLE VI

Samples of the polyurethane foams prepared in Examples III to V were tested for flammability according to the following procedure. A sample of each foam was mounted in a vertical chimney with a wire glass front and ignited with a Bunsen burner for 10 seconds. The duration of the flame after removal of the burner and the percent by weight retained by each foam sample were recorded.

| | Percent Weight Retention | Average Extinguish Time, seconds |
| --- | --- | --- |
| Example III | 82.5 | 0 |
| Example IV | 78.4 | 0.6 |
| Example V (control) | 73.0 | 0.8 |

A comparison of these properties reveals that the addition products of this invention are effective flame retardants for plastic foams such as polyurethane foams, i.e., less foam is consumed with shorter extinguishing times.

While the invention has been described in considerable detail, we do not wish to be limited to the particular embodiments shown and described, and it is our intention to cover hereby all novel adaptions, modifications and arrangements thereof which come within the practice of those skilled in the art to which the invention relates.

6. A polyurethane foam composition according to claim 1 wherein the flame retardant material is represented by the formula:
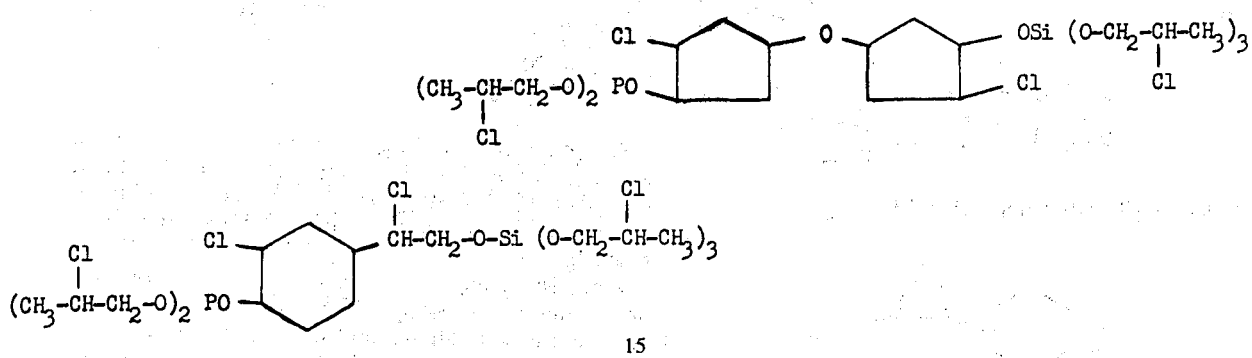

We claim:

1. A polyurethane foam composition formed by reacting, in an NCO/OH index ranging from 1/1 to 5/4, one or more compounds having reactive-NCO groups with one or more polyol having reactive —OH groups; the polyurethane foam composition containing, by weight, 0.5 to 25 percent, based on the total weight of the foam compositions, of a flame retardant material represented by the formula:

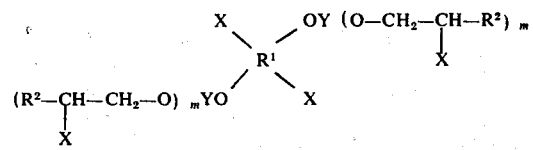

wherein $R^1$ is a divalent group selected from alkyl, alkoxy, cycloalkyl, cycloalkoxy, aryl an ester represented by the formula

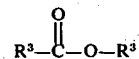

wherein each $R^3$ is alkyl, alkoxy, cycloalkyl, cycloalkoxy or aryl, each $R^3$ having 1 to 20 carbon atoms, or an ether represented by the formula $R^3 — O — R^3$ wherein $R^3$ is as defined above, or a combination thereof, each radical having from 1 to 20 carbon atoms; each $R^2$ is an alkyl radical having 1 to 20 carbon atoms, each X is chlorine, bromine, fluorine or iodine; one of Y is phorphorous and the other Y is silicon and each $m$ is the integer 2 when Y is phosphorus and the integer 3 when Y is silicon.

2. A polyurethane foam composition according to claim 1 wherein the percent by weight, of the flame retardant material ranges from 5 to 15.

3. A polyurethane foam composition according to claim 1 wherein each X is chlorine or bromine and each $R^2$ is an alkyl radical having 1 to 8 carbon atoms.

4. A polyurethane foam composition according to claim 1 wherein the flame retardant material is prepared from a polyepoxide having at least 2 epoxide groups in the polyepoxide before an addition reaction is carried out.

5. A polyurethane foam composition according to claim 1 wherein the flame retardant material is represented by the formula: